(12) United States Patent
Eyssa

(10) Patent No.: US 6,842,324 B2
(45) Date of Patent: Jan. 11, 2005

(54) APPARATUS AND METHOD FOR CONTROLLING MOVEMENT OF AN OBJECT THROUGH A MEDIUM USING A MAGNETIC FIELD

(75) Inventor: Yehia M. Eyssa, Tallahassee, FL (US)

(73) Assignee: FSU Research Foundation, Inc., Tallahassee, FL (US)

( * ) Notice: Subject to any disclaimer, the term of this patent is extended or adjusted under 35 U.S.C. 154(b) by 323 days.

(21) Appl. No.: 10/107,920

(22) Filed: Mar. 27, 2002

(65) Prior Publication Data

US 2002/0186520 A1 Dec. 12, 2002

Related U.S. Application Data

(60) Provisional application No. 60/281,860, filed on Apr. 5, 2001.

(51) Int. Cl.[7] ............................................... H01H 47/00
(52) U.S. Cl. ........................... 361/141; 361/88; 361/91; 361/102; 361/14; 361/117; 335/151; 335/154
(58) Field of Search ........................... 361/141, 88, 91, 361/102, 111, 117; 335/151, 154

(56) References Cited

U.S. PATENT DOCUMENTS

| 3,982,722 A | * | 9/1976 | Bernard ......................... 251/4 |
| 4,813,390 A | * | 3/1989 | Bennett ...................... 123/577 |
| 4,869,247 A | | 9/1989 | Howard, III et al. |
| 4,922,370 A | * | 5/1990 | Mulshine et al. ............. 361/88 |
| 5,125,888 A | | 6/1992 | Howard et al. |
| 5,654,864 A | | 8/1997 | Ritter et al. |
| 6,015,414 A | | 1/2000 | Werp et al. |
| 6,128,174 A | | 10/2000 | Ritter et al. |

* cited by examiner

*Primary Examiner*—Dean A. Reichard
*Assistant Examiner*—Anton Harris
(74) *Attorney, Agent, or Firm*—Senniger Powers

(57) ABSTRACT

Apparatus and method for controlling movement of an object through a medium using a magnetic field by combining the magnetic field of a primary electromagnetic coil having a central axis with the magnetic fields of a plurality of secondary electromagnetic coils having axes generally parallel to the central axis of the primary coil and positioned within the primary coil to produce an operational magnetic field by which movement of the object in a medium is controlled outside of the primary coil.

20 Claims, 11 Drawing Sheets

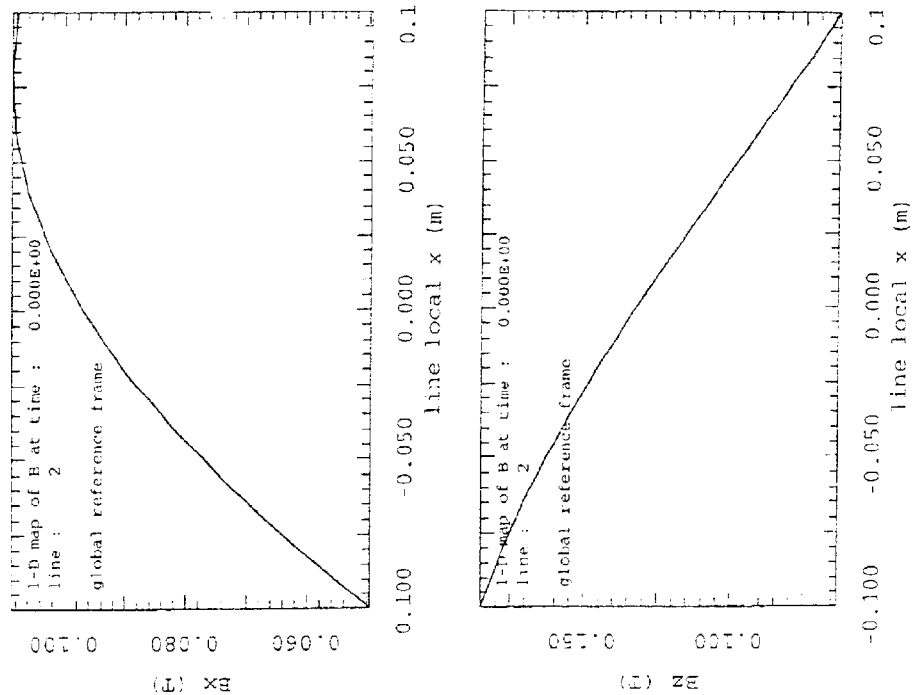
FIG. 4  FIG. 6
FIG. 5  FIG. 7
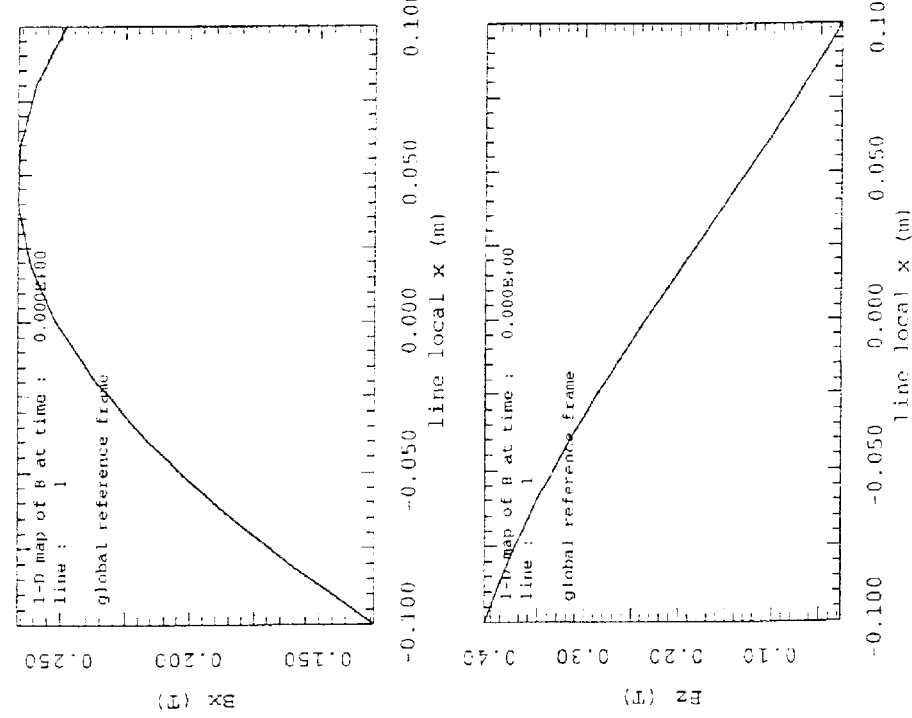

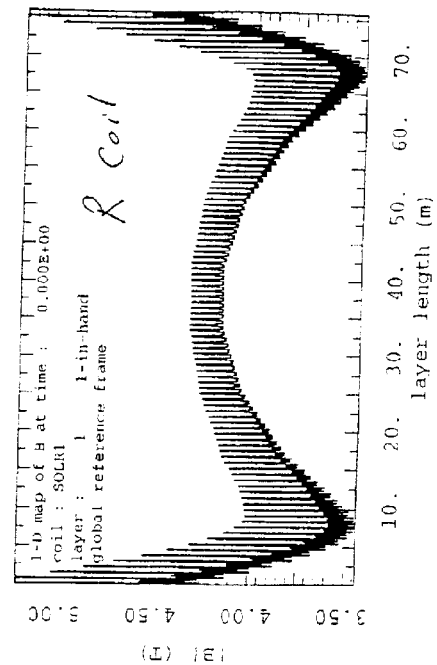
FIG. 9
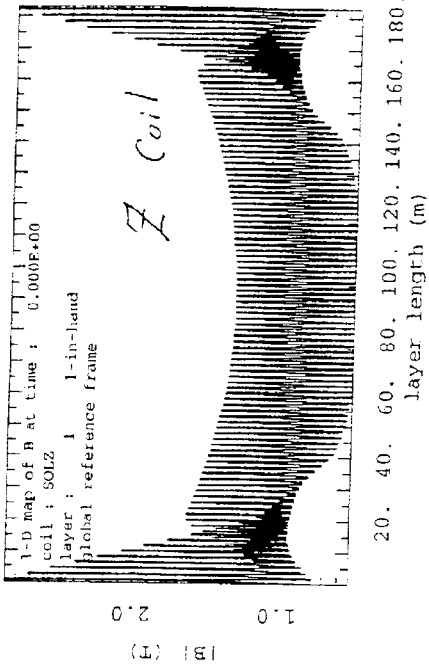
FIG. 10
FIG. 11
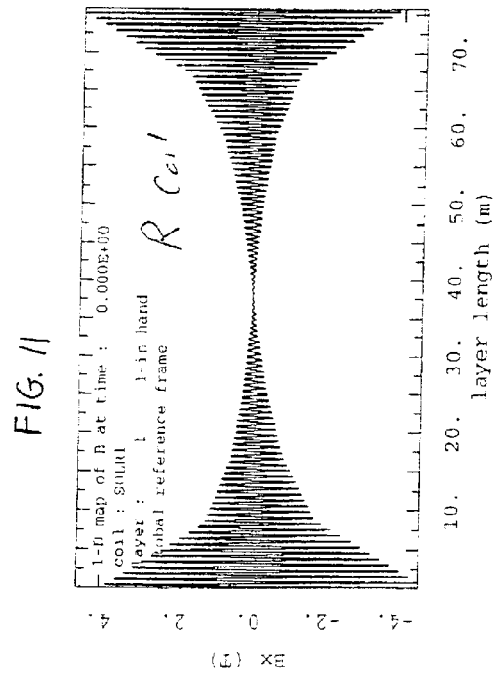
FIG. 12

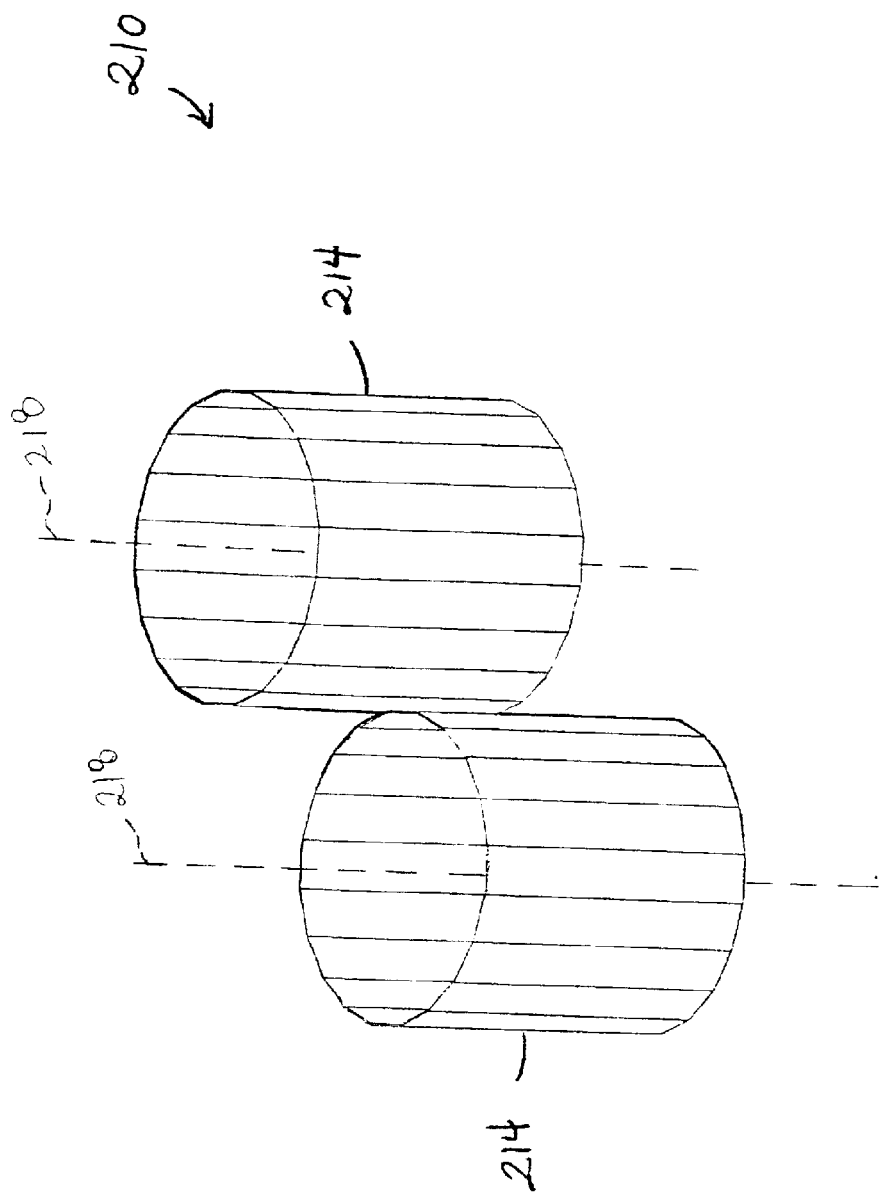

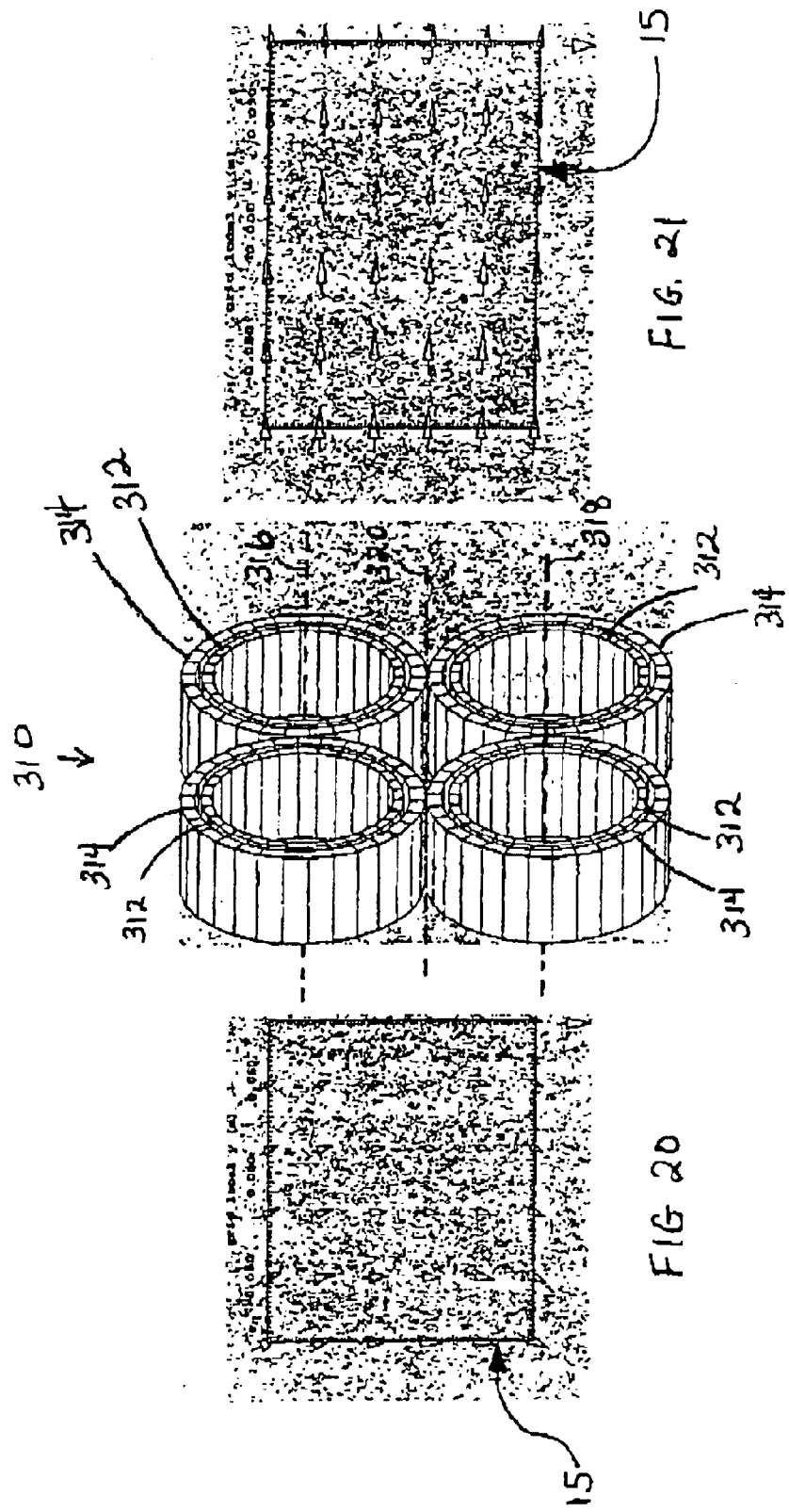

R coil-pair field at r =0.0, 1.5, and 3.0 inches (J=140 A/mm2)- 40" sq

APPARATUS AND METHOD FOR CONTROLLING MOVEMENT OF AN OBJECT THROUGH A MEDIUM USING A MAGNETIC FIELD

BACKGROUND OF THE INVENTION

The present invention relates generally to moving an object through a medium using a magnetic field and, more particularly, to an apparatus and method for controlling the movement of an object through a medium using a magnetic field produced by energized coils by controlling the current in the coils to vary the magnetic field.

The use of a magnetic field to move objects through a medium is known in the prior art. This type of technology has been used in stereotaxic applications to direct instruments, implants and medication to a specific locus in the brain. Examples of such stereotaxic applications are described in U.S. Pat. No. 6,128,174 (Ritter et al.), U.S. Pat. No. 6,015,414 (Werp et al.), U.S. Pat. No. 5,654,864 (Ritter et al.), U.S. Pat. No. 5,125,888 (Howard et al.), and U.S. Pat. No. 4,869,247 (Howard, III et al.), the entire disclosures of which are incorporated herein by reference. In prior stereotaxic applications, however, the magnetic field for moving the object through a patient's body part is changed by either moving the magnet around the patient's body part or by moving the patient. These methods are impractical, especially where large magnets are used to obtain higher magnetic fields. Another prior art method includes placing the patient's head within an electromagnetic coil or between a number of electromagnetic coils and changing the coils' current magnitude and direction. This method is impractical because the coil restricts access to the patient's head, which impedes surgery.

As recognized by the inventor hereof, what is needed is a cost effective apparatus and method that controls the movement of an object through a medium, such as a patient's brain, using a variable magnetic field produced by a magnet at a certain range from a patient such that neither the magnet nor patient need to be moved and such that access to the patient is not impeded by the magnet apparatus.

SUMMARY OF THE INVENTION

The inventor hereof has designed and developed an apparatus and method for controlling the movement of an object through a medium using a variable magnetic field produced at a certain range from a patient such that neither the magnet nor patient need to be moved in order to change the magnetic field, and such that access to the patient is not impeded by the magnet. In general, the magnetic field of a primary electromagnetic coil having a central axis combines with the magnetic fields of a plurality of secondary electromagnetic coils having axes generally parallel to the central axis of the primary coil and positioned within the primary coil to produce an operational magnetic field for controlling movement of an object in a medium outside of the primary coil. The object is moved by varying the current through the electromagnetic coils to obtain the desired magnetic field in any direction without the necessity for any mechanical movements of the apparatus or patient.

In accordance with one aspect of the present invention, an apparatus for producing a variable magnetic field for controlling movement of an object in a medium includes a primary electromagnetic coil having a central axis and producing a magnetic field when energized with current. The apparatus also includes a plurality of secondary electromagnetic coils positioned within the primary coil, each secondary coil having a central axis generally parallel to the central axis of the primary coil and producing a magnetic field when energized with current. The magnetic fields of the primary and secondary coils combine to produce an operational magnetic field for controlling movement of the object in the medium located outside of the primary coil. A current source for energizing the primary and secondary coils controls the current in the primary and secondary coils to vary the direction and magnitude of the operational magnetic field for controlling movement of the object in the medium.

In accordance with another aspect of the present invention, an apparatus for producing a variable magnetic field for controlling movement of an object in a medium includes a plurality of electromagnetic coils positioned generally adjacent each other and having generally parallel axes. Each of the plurality of electromagnetic coils produces an operational magnetic field when energized with current. The magnetic fields of the plurality of coils combine to produce an operational magnetic field for controlling movement of the object in the medium outside the plurality of coils. A current source for energizing the plurality of coils controls the current in the plurality of coils to vary the direction and magnitude of the operational magnetic field for controlling movement of the object in the medium.

In accordance with yet another aspect of the present invention, a method of producing a variable magnetic field for controlling movement of an object in a medium includes the steps of positioning a primary electromagnetic coil having a central axis around a plurality of secondary electromagnetic coils each having a central axis generally parallel to the central axis of the primary coil. The primary and secondary coils each produce a magnetic field when energized with current and the magnetic fields of the primary and secondary coils combine to produce an operational magnetic field for controlling movement of the object in the medium. The method further includes positioning the object in the medium outside of the primary coil and at a distance from the primary and secondary coils and applying currents to the primary and secondary coils to vary the direction and magnitude of the operational magnetic field for controlling movement of the object in the medium.

Other features and advantages of the present invention will be in part apparent and in part pointed out hereinafter.

BRIEF DESCRIPTION OF THE DRAWINGS

FIGS. 4 and 5 are exemplary graphs of the magnetic fields in the transverse and axial directions, respectively, at approximately nine inches for the apparatus of FIG. 1.

FIGS. 6 and 7 are exemplary graphs of the magnetic fields in the transverse and axial directions, respectively, at approximately fourteen inches for the apparatus of FIG. 1.

FIG. 9 is an exemplary graph illustrating aspects of the magnetic field of the primary electromagnetic coil of FIG. 8.

FIG. 10 is an exemplary graph illustrating aspects of the magnetic field of one of the secondary electromagnetic coils of FIG. 8.

FIGS. 11 and 12 are exemplary graphs illustrating aspects of the magnetic fields in the transverse and axial directions, respectively, of one of the secondary electromagnetic coils of FIG. 8.

FIG. 17 illustrates an apparatus having two electromagnetic coils positioned generally adjacent each other according to another preferred embodiment of the invention.

FIG. 18 is an exemplary graph of the magnetic field profile for the electromagnetic coils of FIG. 17.

FIG. 19 illustrates an apparatus having four secondary electromagnetic coils surrounding four primary electromagnetic coils according to another preferred embodiment of the invention.

FIGS. 20 and 21 are exemplary graphs of the transverse and axial magnetic field profile for the electromagnetic coils of FIG. 19.

DETAILED DESCRIPTION OF PREFERRED EMBODIMENTS

Figure 1:
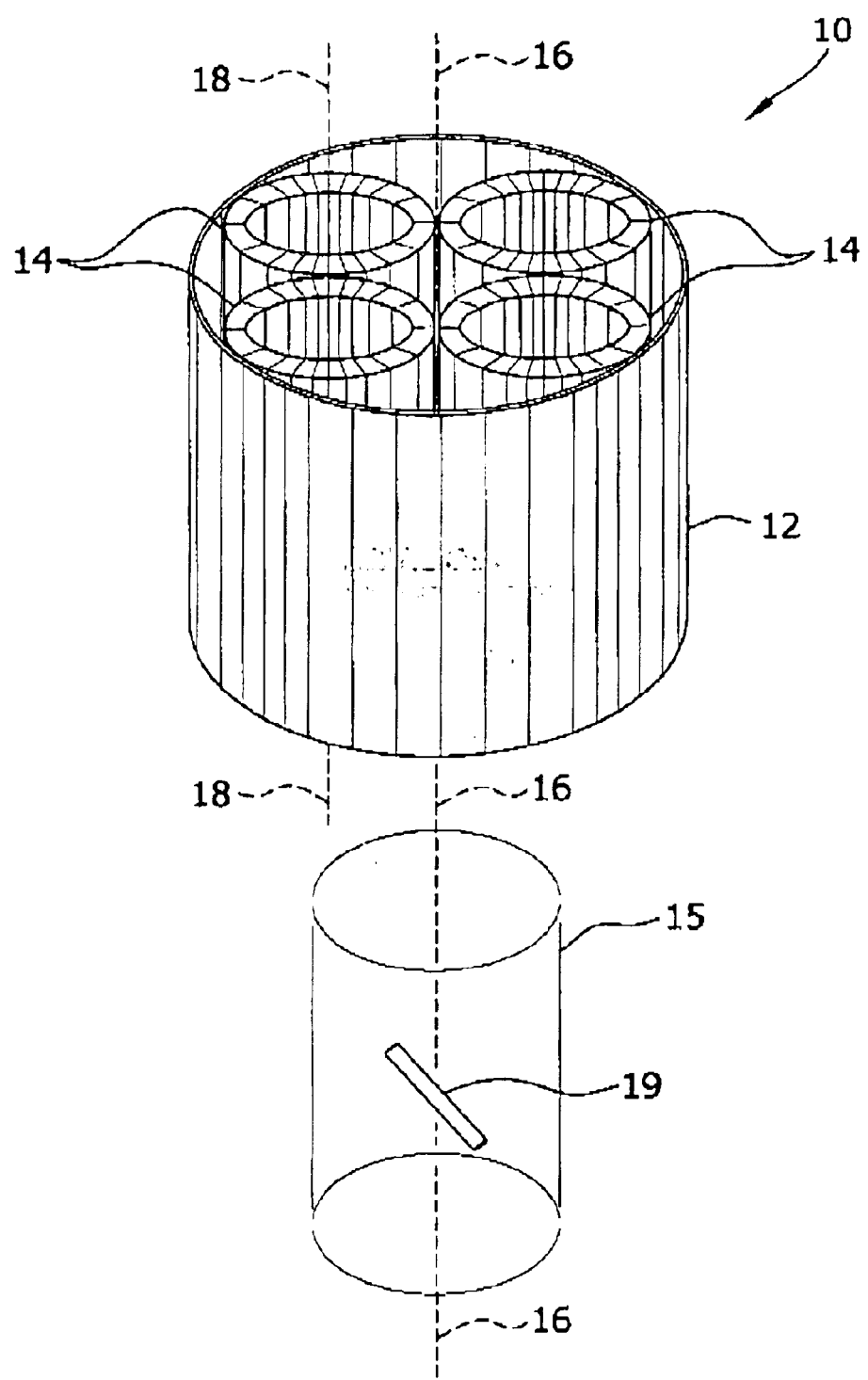
FIG. 1 illustrates an apparatus having primary electromagnetic coil surrounding four secondary electromagnetic coils according to a preferred embodiment of the invention.

Referring now to the drawings, an apparatus according to one preferred embodiment of the present invention is shown in FIG. 1 and is designated generally by reference character 10. A primary electromagnetic coil 12 has a central axis 16 and produces a magnetic field when energized with current. A plurality of secondary coils 14 are positioned within the primary coil 12. The secondary coils 14 each have a central axis 18 generally parallel to the central axis 16 of the primary coil 12. The secondary coils 14 also each produce a magnetic field when energized with current. The electromagnetic coils are preferably superconducting and comprise permeable and/or holmium cores. The primary electromagnetic coil 12 preferably has a thirty inch or forty inch outside diameter. For simplicity, only one central axis 18 is illustrated in FIG. 1.

In operation of this embodiment, three current sources (not shown) energize the primary coil 12 and the secondary coils 14 to produce a magnetic field at each coil. There are three electrical circuits fed by three current sources; one circuit for the primary magnet and two circuits for the four secondary magnets (working as two pairs). The two radial coil pairs work in a way to rotate the radial field in any radial direction. Magnetic fields of primary coil 12 and secondary coils 14 combine to produce an operational magnetic field for controlling movement of an object 19 in a medium 15 outside of the primary coil 12. Primary coil 12 provides a generally axial component of the operational magnetic field relative to its central axis 16. The magnetic fields of the secondary coils 14 provide a generally radial component of the operational magnetic field also relative to the central axis 16 of the primary coil 12. By varying the current in primary coil 12 and/or the two currents of the secondary coils 14, the direction and magnitude of the operational magnetic field can be changed to obtain a desired magnetic field strength at a desired distance from the coils. An operator preferably controls the currents in primary coil 12 and secondary coils 14 to vary the direction and magnitude of the operational magnetic field to control the movement of an object through a medium at some distance from the apparatus 10. An example of an object is a permanent magnet in the form of a needle about 2 mm long and 1 mm in diameter made of strong permanent magnet material. The object would be located in a cylindrical volume of an about 6" diameter or less and is located between 9" and 14" from the top of the magnets. The axis of the cylindrical volume coincides with the axis of the magnet system.

As shown in FIG. 1, in one preferred embodiment of the invention, the plurality of secondary coils 14 comprise four electromagnetic coils generally adjacent each other and forming two magnet pairs that are fed from two different current sources. The four electromagnetic coils 14 are symmetrically positioned around the central axis 16 of primary coil 12 inside the bore defined by an inner surface of the primary coil.

Figure 3:
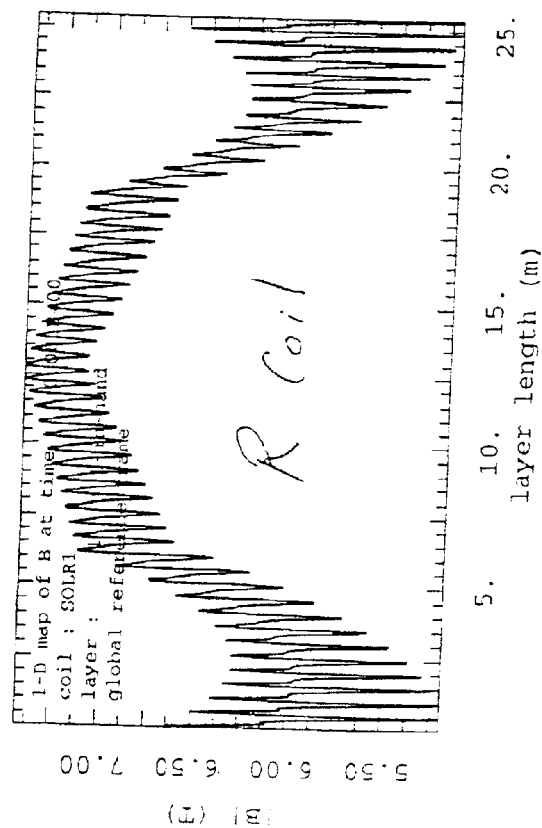
FIG. 3 is an exemplary graph illustrating aspects of the magnetic field of one of the secondary electromagnetic coils of FIG. 1.
Figure 2:
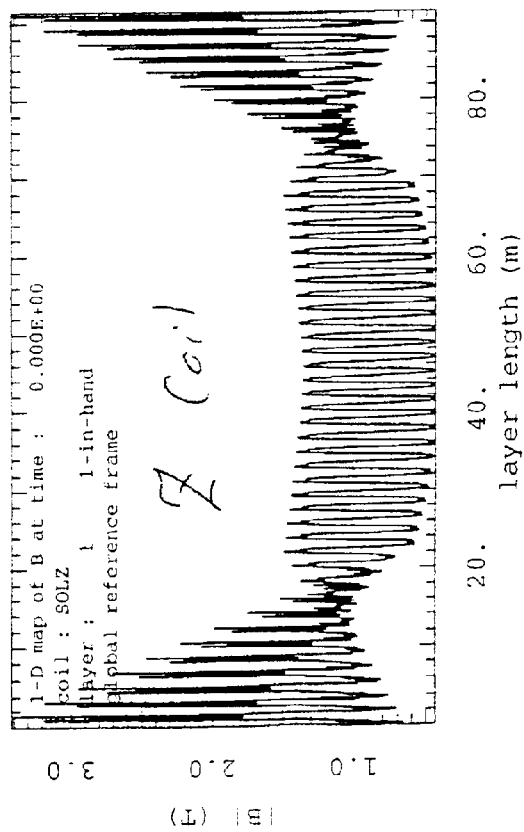
FIG. 2 is an exemplary graph illustrating aspects of the magnetic field of the primary electromagnetic coil of FIG. 1.

FIG. 2 illustrates aspects of the magnetic field of the primary electromagnetic coil 12 of FIG. 1. FIG. 3 illustrates aspects of the magnetic field of one of the secondary electromagnetic coils 14 of FIG. 1. In this instance, magnetic field magnitude is shown relative to layer length. Layer length is the length of the helical winding in any particular layer (the most inner layer is shown here) assuming the coil is layer wound coil. The field at the winding is shown over one whole layer length. The maximum field value indicates the type of superconductor wire that can be used to generate the desired field at the magnetic object 19 in the patient's body.

FIGS. 4 and 5 are graphs of the magnetic fields for the apparatus 10 of FIG. 1 in the transverse and axial directions, respectively, at approximately nine inches from the top of the coil's winding. FIGS. 6 and 7 are graphs of the magnetic fields for the apparatus 10 of FIG. 1 in the transverse and axial directions, respectively, at approximately fourteen inches from the top of the coil's winding.

As shown in FIGS. 4, 5, 6, and 7, the three field components Bz (axial field), Bx or By (transverse or radial field) due to either the primary magnet alone or one pair of the secondary magnets are shown over a desired cylindrical volume. As shown, the primary magnet produces only a pure axial field on axis. Off axis it produces a small radial field. The opposite occurs due to the radial magnets. The currents in the three circuits are controlled so that the desired field can be produced in any direction within the working cylindrical volume.

Figure 8:
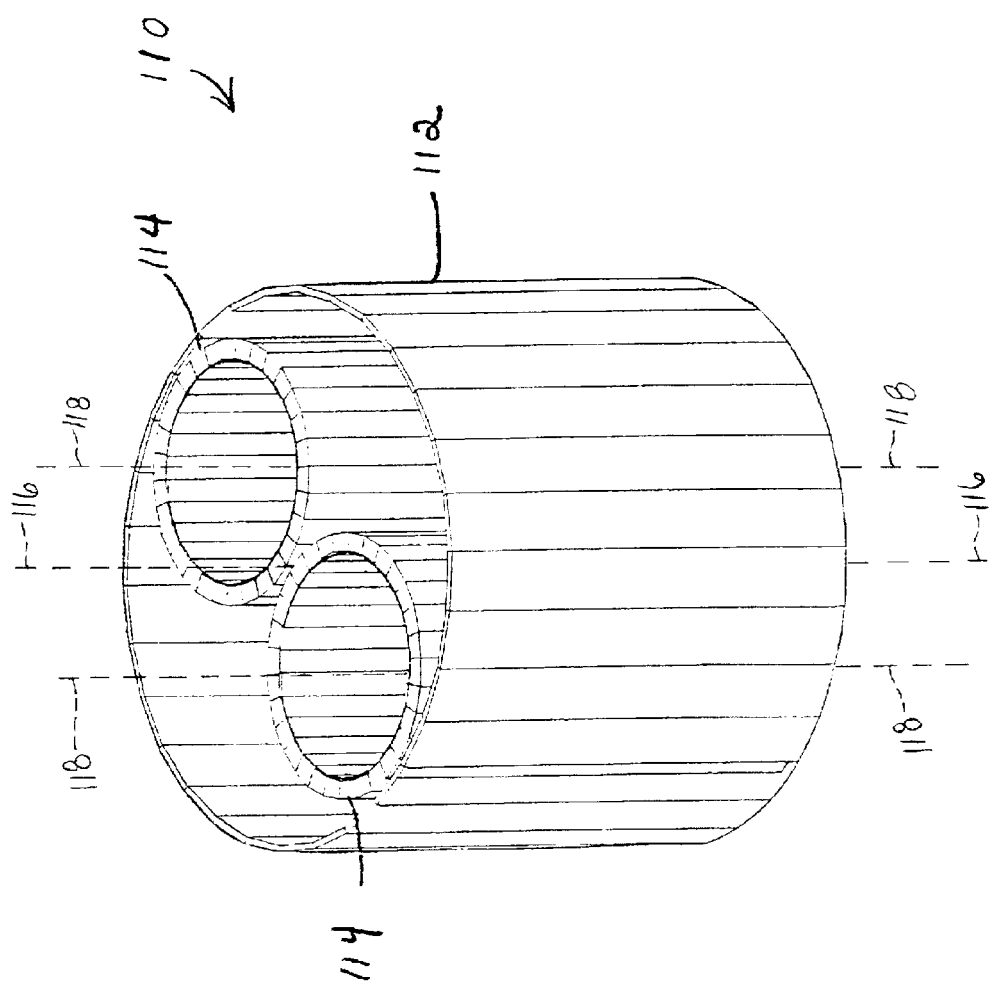
FIG. 8 illustrates an apparatus having a primary electromagnetic coil surrounding two secondary electromagnetic coils according to another preferred embodiment of the invention.

An apparatus according to another preferred embodiment of the present invention is shown in FIG. 8 and is designated generally by reference character 110. In this preferred embodiment, two secondary electromagnetic coils 114 are positioned within a primary coil 112. The secondary electromagnetic coils 114 each have a central axis 118 generally parallel to a central axis 116 of the primary coil 112. The primary coil 112 and the secondary coils 114 each produce a magnetic field when energized with current.

The operation of this embodiment is similar to the embodiment described above. Two current sources (not shown) energize the primary coil 112 and the secondary coils 114 to produce a magnetic field in one plane inside the working volume. The system mechanically rotates around its axis so that the radial field can point to any desired direction. As in the above described embodiment, the magnetic fields of primary coil 112 and secondary coils 114 in addition to the mechanical rotation of the magnet system combine to produce an operational magnetic field for controlling movement of an object in a medium outside of the primary coil 112. Primary coil 112 provides a generally axial component of the operational magnetic field relative to its central axis 116 and the magnetic fields of the secondary coils 114 provide a generally radial component of the operational magnetic field also relative to the central axis 116 of the primary coil. By varying the current in the primary coil 112 and/or secondary coils 114 in addition to the mechanical rotation of the magnet system, the direction and magnitude of the operational magnetic field can be changed to obtain a desired magnetic field strength at a desired distance from the coils. An operator preferably controls the current in the primary coil 112 and secondary coils 114 to vary the direction and magnitude of the operational magnetic field to control movement of an object in a medium at some distance from the apparatus 110.

FIG. 9 illustrates aspects of the magnetic field of the primary electromagnetic coil 112 of FIG. 8. FIG. 10 illustrates aspects of the magnetic field of one of the secondary electromagnetic coils 114 of FIG. 8. In this instance magnetic field magnitude is shown relative to layer length. Layer length is the length of the helical winding in any particular layer (the most inner layer is shown here) assuming the coil is layer wound coil. The field at the winding is shown over one whole layer length. The maximum field value indicates the type of superconductor wire that can be used to generate the desired field at the magnetic object in the patient's body.

Figure 13:
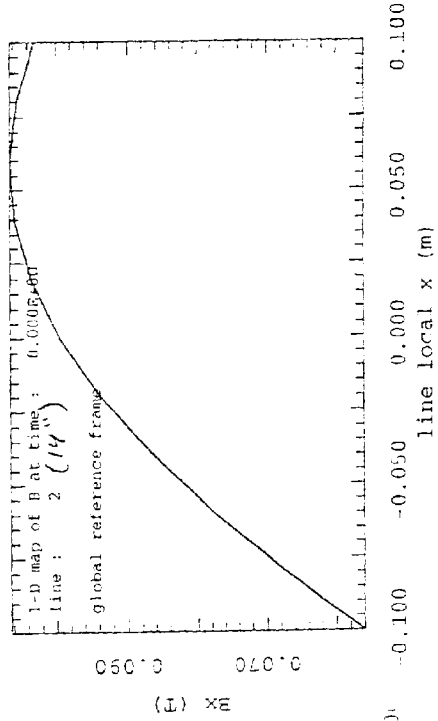
FIGS. 13 and 14 are exemplary graphs of the magnetic fields in the transverse and axial directions, respectively, at approximately nine inches for the apparatus of FIG. 8.
Figure 15:
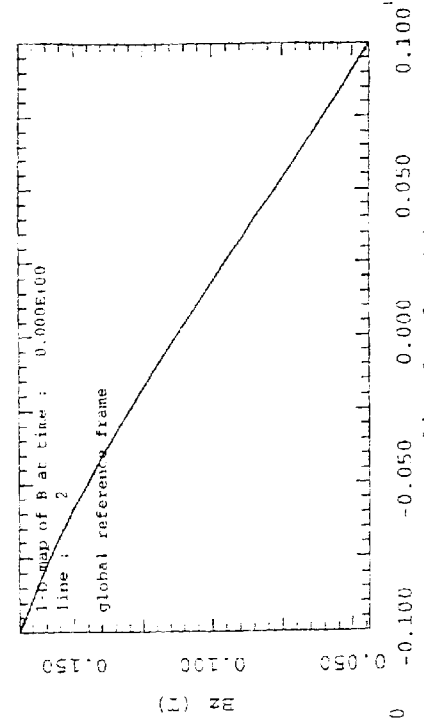
FIGS. 15 and 16 are exemplary graphs of the magnetic fields in the transverse and axial directions, respectively, at approximately fourteen inches for the apparatus of FIG. 8.
Figure 14:
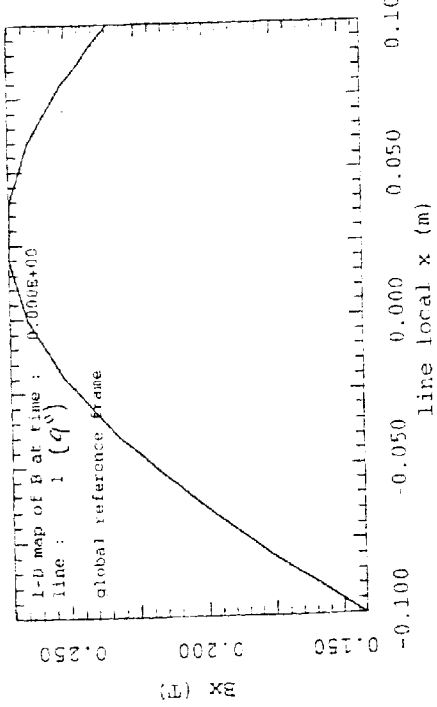
Figure 16:
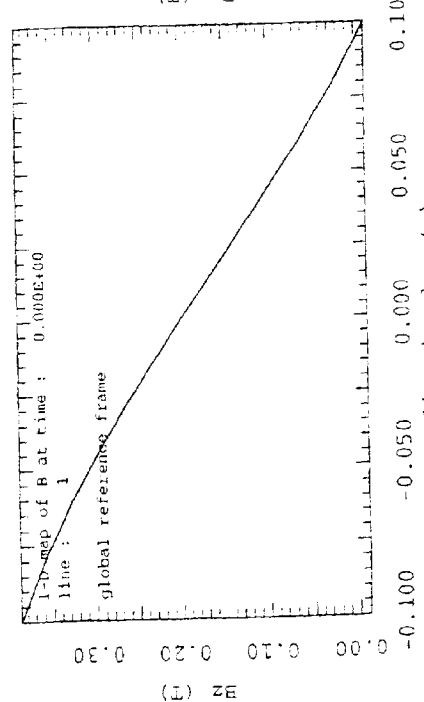
Figure 1B:
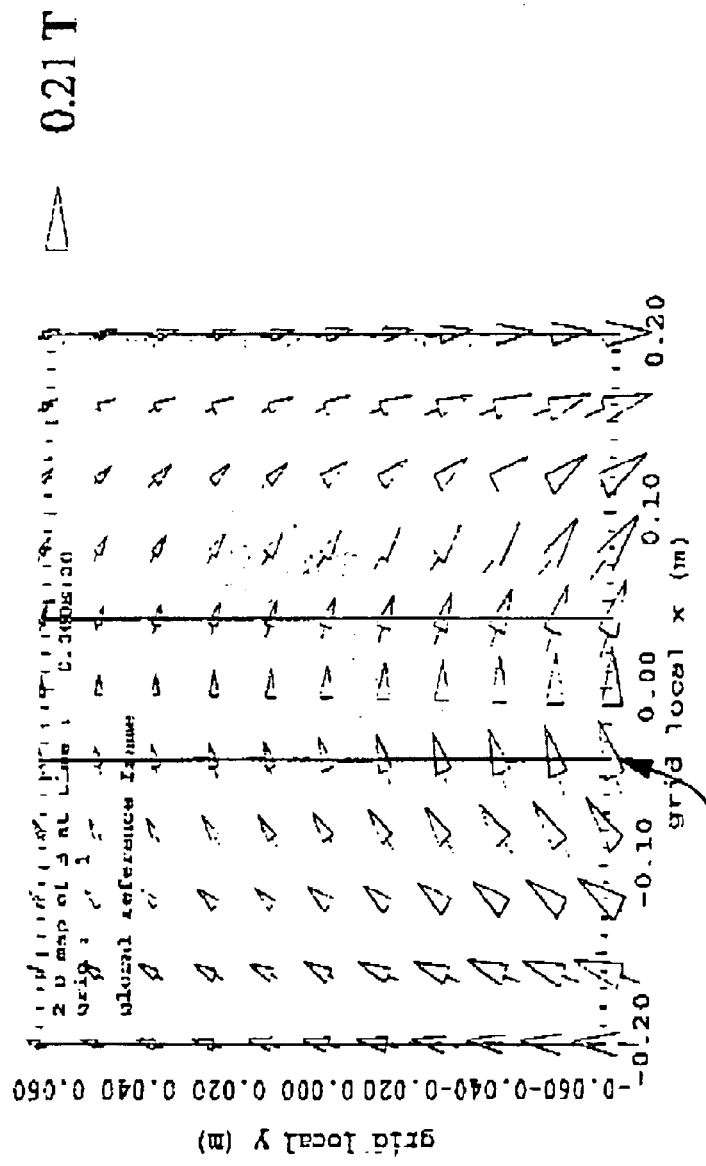

FIGS. 11 and 12 are graphs of the magnetic fields for the apparatus of FIG. 8 in the transverse and axial directions, respectively. FIGS. 13 and 14 are graphs of the magnetic fields for the apparatus 110 of FIG. 8 in the transverse and axial directions, respectively, at approximately nine inches from the top of the coils. FIGS. 15 and 16 are graphs of the magnetic fields for the apparatus 110 of FIG. 8 in the transverse and axial directions, respectively, at approximately fourteen inches from the top of the coils.

As shown in FIGS. 11–16, the three field components Bz (axial field), Bx or By (transverse or radial field) due to either the primary magnet alone or one pair of the secondary magnets are shown over a desired cylindrical volume. As shown, the primary magnet produces only a pure axial field on axis. Off axis it produces a small radial field. The opposite occurs due to the radial magnets. The currents in the three circuits are controlled so that the desired field can be produced in any direction within the working cylindrical volume.

An apparatus according to another preferred embodiment of the present invention is shown in FIG. 17 and is designated generally by reference character 210. In this preferred embodiment, a plurality of electromagnetic coils 214 having generally parallel axes 218 are positioned generally adjacent each other. As shown in FIG. 17, the plurality of coils preferably comprises two electromagnetic coils connected electrically in series and powered by one current source. The coil pair 214 produces a magnetic field when energized with current. The combination of the coils' translation and rotation and their magnetic fields produce an operational magnetic field for controlling movement of the object in the medium outside the plurality of coils. In operation, one current source energizes the plurality of coils 214 to produce a magnetic field at each coil. By varying the current in the plurality of coils 214, the magnitude of the operational it magnetic field can be changed to obtain a desired magnetic field strength at a desired distance from the coils. The direction of the desired field is varied through the translation of the two coil pair and their rotation around their axis similar to the permanent magnet system used by, for example, STEREOTAXIS, Inc. The difference is that the two coil pair (operated by one current source or in persistent mode) produce a much stronger field than a permanent magnet system. An operator preferably controls the current in the plurality of coils 214 and their position to vary the direction and magnitude of the operational magnetic field to control movement of an object in a medium at a distance from the plurality of coils 214.

FIG. 18 is a graph of the magnetic field profile for the electromagnetic coils of FIG. 17. As shown in FIG. 18, the field vector can have any direction up or down in the axial direction or purely transverse or a combination of both, so its magnitude and direction can be varied through the relative magnet to the patient positioning only, in addition to the possibility of varying the current value.

Referring now to FIG. 19, an apparatus according to yet another preferred embodiment of the present invention is designated generally by reference character 310. In this embodiment, a plurality of primary electromagnetic coils 312 provide a generally axial component of an operational magnetic field. A plurality of secondary electromagnetic coils 314 provide a generally radial component of the operational magnetic field. The secondary electromagnetic coils 314 have generally parallel central axes 318 and are positioned generally adjacent each other. Secondary electromagnetic coils 314 powered by two separate current sources form two coil pairs, wherein each pair produces a mainly transverse or radial magnetic field when energized from a current source. An equal number of primary electromagnetic coils 312 are positioned such that one primary electromagnetic coil 312 is positioned within each secondary coil 314. The primary coils 312 each have a central axis 316 generally parallel to the generally parallel axes of the secondary coils 314. The primary coils 312 are all electrically connected in series and produce a mainly axial magnetic field when energized from a single current source.

As shown in FIG. 19, in this preferred embodiment the plurality of coils preferably has N primary electromagnetic coils 312 positioned within N secondary electromagnetic coils 314. In this instance, N equals four. The four secondary coils 314 are symmetrically positioned around a central axis 320. The width of the plurality of coils as positioned in this embodiment is preferably forty inches or less. One skilled in the art will recognize that this preferred embodiment can be conveniently used in a square dewar having a forty inch top to bottom warm dimension.

The magnetic fields of the coils 312 and 314 combine to produce an operational magnetic field for controlling movement of an object in a medium outside the plurality of coils. A current source energizes the plurality of the single circuit coils 312 and the two circuit two coil pairs 314 to produce magnetic fields in each coil. The primary coils 312 provide a generally axial component of the operational magnetic field and the secondary coils 314 provide a generally radial component of the operational magnetic field. The three current sources control the current in the plurality of the one circuit coils 312 and the two circuit two coil pairs 314 to vary the direction and magnitude of the operational magnetic field for controlling movement of an object in a medium at a distance from the plurality of coils.

FIGS. 20 and 21 are graphs of the transverse and axial field profile for the electromagnetic coils of FIG. 19.

Figure 22:
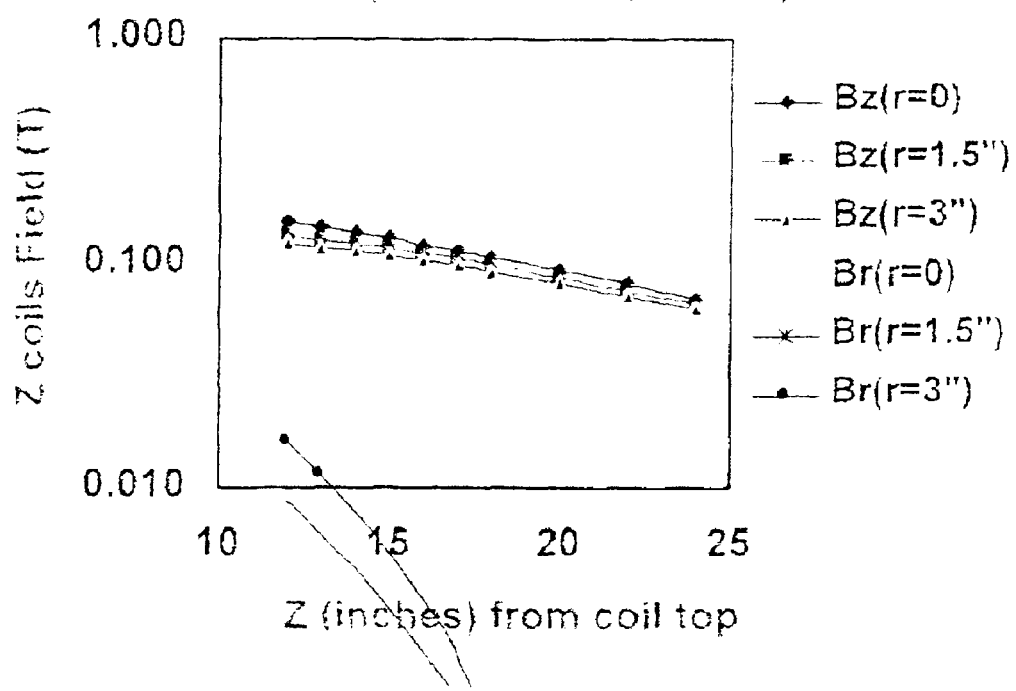
FIGS. 22 and 23 are exemplary graphs of the radial (transverse) and axial field profile for the electromagnetic coils of FIG. 19.
Figure 23:
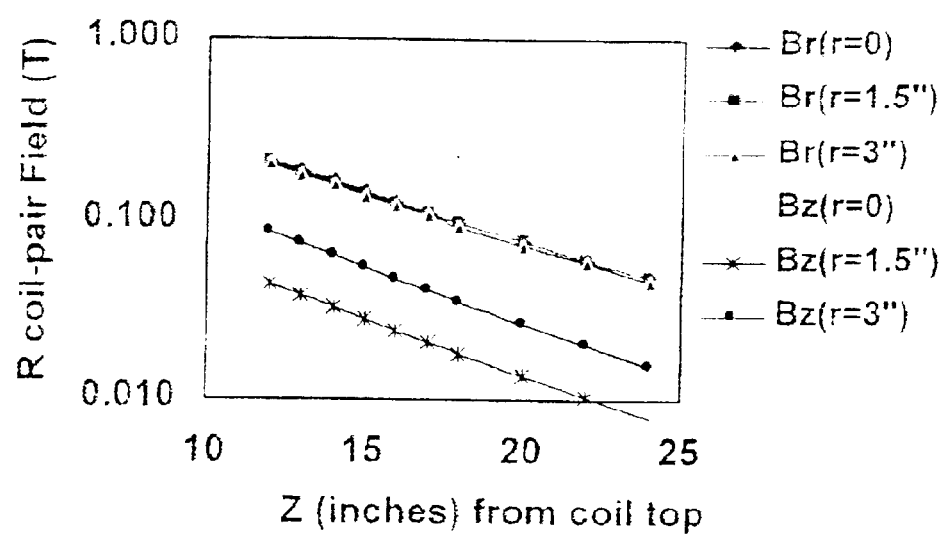

FIGS. 22 and 23 are graphs of the magnetic field profile for the electromagnetic coils of FIG. 19. FIG. 22 shows the axial and radial field produced by the axial coils 312 at an axial position of 12–24" from the apparatus midplane and at different radii from the system axis. As shown the field is mostly axial with very small radial field at off axis position. FIG. 23 shows the axial and radial field produced by the 5 radial coils 314 at an axial position of 12–24" from the apparatus midplane tops and at different radii from the system axis. As shown the field is mostly radial with a small axial field at off axis position. It is relatively easy using these graphs to calculate the three circuit currents that produce a desired magnitude and direction magnetic field.

Table I provides a summary identifying the system parameters for the electromagnetic coils square of FIG. 19. in comparison with the circular electromagnet system of FIG. 1. In the Table, all system parameters are based on B=0.1 T at z=17" and r=3".

each secondary coil having a central axis generally parallel to the central axis of the primary coil and producing a transverse magnetic field when energized with current. The magnetic fields of the primary and secondary coils combine to produce an operational magnetic field for controlling movement of the object in the medium located outside of the primary coil. A current source for energizing the primary and secondary coils controls the current in the primary and secondary coils to vary the direction and magnitude of the operational magnetic field for controlling movement of the object in the medium.

When introducing elements of the present invention of the preferred embodiments thereof, the articles "a", "an", "the" and "said" are intended to mean that there are one or more of the elements. The terms "comprising", "including" and "having" are intended to be inclusive and meant that there may be additional elements other than the listed elements.

| System<br>System OD (inches) | FIG. 1<br>35 | FIG. 1<br>40 | FIG. 1<br>45 | FIG. 1<br>50 | FIG. 19<br>40" square |
|---|---|---|---|---|---|
| Winding height (cm) | 40 | 30 | 25 | 21 | 22 |
| Winding mass (kg) | 354.2 | 272.1 | 217.3 | 187.1 | 242.4 |
| R coil maximum field (T) | 9.467 | 6.209 | 4.574 | 3.741 | 3.740 |
| Z coil maximum field (T) | 1.134 | 0.995 | 0.997 | 0.992 | 2.240 |
| one R coil pair amperemeters (Am) | 4.995E+ | 3.283E+06 | 2.525E+0 | 2.101E+06 | 2.126E+06 |
| one Z coil amperemeters (Am) | 2.090E+ | 1.815E+06 | 1.743E+0 | 1.741E+06 | 6.789E+05 |
| All coils amperemeters (Am) | 1.208E+ | 8.381E+06 | 6.793E+0 | 5.944E+06 | 6.968E+06 |
| R coil pair energy (kJ) | 950.0 | 580.0 | 390.0 | 292.0 | 270.0 |
| Z coils energy (kJ) | 75.8 | 54.7 | 56.8 | 53.5 | 202 |
| Charging time (s) | 20 | 20 | 20 | 20 | 20 |
| R coil pair charging voltage (V) based | 992.8 | 564.4 | 371.0 | 273.6 | 263.3 |
| Z coils charging voltage (V) based on | 74.29 | 56.93 | 55.79 | 53.98 | 202.00 |
| R coil pair maximum current (A) | 104.50 | 97.31 | 95.14 | 93.70 | 97.50 |
| Z coil maximum current (A) | 98.01 | 104.08 | 98.23 | 100.9 | 104.43 |
| R coil inner radius (m) | 0.102 | 0.138 | 0.173 | 0.203 | 0.195 |
| R coil outer radius (m) | 0.152 | 0.178 | 0.205 | 0.231 | 0.222 |
| R coil center radius (m) | 0.218 | 0.255 | 0.292 | 0.329 | 0.316 |
| R Coil number of turns (one coil) | 30000 | 17010 | 11200 | 8232 | 8316 |
| R coil current density (A/mm2) | 156.8 | 136.2 | 133.2 | 131.2 | 136.5 |
| Z coil inner radius (m) | 0.374 | 0.437 | 0.501 | 0.564 | 0.165 |
| Z coil outer radius (m) | 0.381 | 0.445 | 0.508 | 0.572 | 0.183 |
| Z coil center radius (m) | 0.000 | 0.000 | 0.000 | 0.000 | 0.316 |
| Z coil number of turns | 4500 | 3150 | 2800 | 2419 | 5940 |
| Z coil current density (A/mm2) | 147.0 | 145.7 | 157.2 | 161.4 | 156.7 |
| R coil Pair charge ac loss/cycle | 500.0 | 350.0 | 300.0 | 250.0 | 312.0 |
| Z coils charge ac loss/cycle (J) | 200.0 | 150.0 | 119.8 | 103.2 | 205.0 |
| Average loss per cycles = [2 * R + Z]/3 | 400.0 | 283.3 | 239.9 | 201.1 | 276.3 |
| Estimated power loss for 15 full ramps | 0.8 | 0.6 | 0.5 | 0.4 | 0.6 |
| Estimated power loss for 50 relative | 2.8 | 2.0 | 1.7 | 1.4 | 1.9 |

According to the invention, it is preferred that, in any of the embodiments described above, the electromagnetic coils are superconducting. It is also preferred that the electromagnetic coils comprise permeable cores and may further comprise holmium cores according to the invention. In a preferred embodiment of the invention, the system has a thirty inch or forty inch outside diameter, height or width. Advantageously, the forty inch outside diameter, height or width system provides a sufficient operational magnetic field without magnetic material inside and at reduced winding field. This makes the system easier, simpler, and less expensive to construct. It also allows use of the system in a forty inch square dewar.

In summary, according to one aspect of the invention, an apparatus for producing a variable magnetic field for controlling movement of an object in a medium includes a primary electromagnetic coil having a central axis and producing an axial magnetic field when energized with current. The apparatus also includes a plurality of secondary electromagnetic coils positioned within the primary coil, As various changes could be made in the above constructions without departing from the scope of the invention, it is intended that all matter contained in the above description or shown in the accompanying drawings shall be interpreted as illustrative and not in a limiting sense.

What is claimed is:

1. An apparatus for producing a variable magnetic field for controlling movement of an object in a medium, said apparatus comprising:

a primary electromagnetic coil having a central axis, said primary coil producing a magnetic field when energized with current; and a plurality of secondary electromagnetic coils positioned within the primary coil, said secondary coils each having a central axis generally parallel to the central axis of the primary coil and producing a magnetic field when energized with current, said magnetic fields of the primary and secondary coils combining to produce an operational magnetic field for controlling movement of the object in the medium outside of the primary and secondary coils wherein the currents in the primary and secondary coils are controlled to vary the direction and magnitude of the operational magnetic field for controlling movement of the object in the medium outside of the primary and secondary coils.

2. The apparatus of claim 1 wherein said magnetic field of the primary coil provides a generally axial component of the operational magnetic field relative to the central axis of the primary coil, and said magnetic fields of the secondary coils provides a generally radial component of the operational magnetic field relative to the central axis of the primary coil.

3. The apparatus of claim 1 wherein the plurality of secondary electromagnetic coils comprises four electromagnetic coils generally adjacent each other.

4. The apparatus of claim 3 wherein the four electromagnetic coils are symmetrically positioned around the central axis of the primary electromagnetic coil.

5. The apparatus of claim 1 wherein the plurality of secondary electromagnetic coils comprises two electromagnetic coils generally adjacent each other.

6. The apparatus of claim 1 wherein the primary electromagnetic coil and the secondary electromagnetic coils are superconducting.

7. The apparatus of claim 1 wherein the plurality of secondary electromagnetic coils comprise permeable cores.

8. The apparatus of claim 1 wherein the plurality of secondary electromagnetic coils comprise holmium cores.

9. An apparatus for producing a variable magnetic field for controlling movement of an object in a medium, said apparatus comprising a plurality of electromagnetic coils positioned generally adjacent each other and having generally parallel axes, each of said plurality of electromagnetic coils producing a magnetic field when energized with current, the magnetic fields of the plurality of coils combining to produce an operational magnetic field for controlling movement of the object in the medium outside the plurality of coils wherein the respective currents in the plurality of coils are controlled to vary the direction and magnitude of the operational magnetic field for controlling movement of the object in the medium outside of the plurality of coils.

10. The apparatus of claim 9 wherein the plurality of electromagnetic coils comprises two electromagnetic coils.

11. The apparatus of claim 9 wherein the plurality of electromagnetic coils comprises N primary electromagnetic coils and N secondary electromagnetic coils positioned such that one of each primary electromagnetic coil is positioned within one of each secondary electromagnetic coil.

12. The apparatus of claim 11 wherein N equals four.

13. The apparatus of claim 12 wherein the plurality of secondary coils are symmetrically positioned around a central axis.

14. The apparatus of claim 9 wherein the plurality of electromagnetic coils are superconducting.

15. The apparatus of claim 9 wherein the plurality of electromagnetic coils comprise permeable cores.

16. The apparatus of claim 9 wherein the plurality of electromagnetic coils comprise holmium cores.

17. An apparatus for producing a variable magnetic field for controlling movement of an object in a medium, said apparatus comprising:

N secondary electromagnetic coils positioned generally adjacent each other and having generally parallel axes, each of said secondary electromagnetic coils producing a magnetic field when energized with current; and N primary electromagnetic coils positioned such that one of said N number of primary electromagnetic coils is positioned within one of each of said N secondary electromagnetic coils, each of said primary electromagnetic coils having axes generally parallel to the secondary coils generally parallel axes and producing a magnetic field when energized with current, said magnetic fields of the primary and secondary coils combining to produce an operational magnetic field for controlling movement of the object in the medium outside the plurality of coils wherein the currents in the primary and secondary coils are controlled to vary the direction and magnitude of the operational magnetic field for controlling movement of the object in the medium outside of the plurality of coils.

18. The apparatus of claim 17 wherein N equals four.

19. The apparatus of claim 18 wherein the plurality of secondary coils are symmetrically positioned around a central axis.

20. A method of producing a variable magnetic held for controlling movement of an object in a medium, said method comprising the steps of:

positioning a primary electromagnetic coil having a central axis around a plurality of secondary electromagnetic coils each having a central axis generally parallel to the central axis of the primary coil, said primary and secondary coils each producing a magnetic field when energized with current, said magnetic fields of the primary and secondary coils combining to produce an operational magnetic field for controlling movement of the object in the medium outside of the primary and secondary coils;

positioning the object in the medium outside of the primary and secondary coils and at a distance from said primary and secondary coils; and applying currents to the primary and secondary coils to vary the direction and magnitude of the operational magnetic field for controlling movement of the object in the medium outside of the primary and secondary coils.

* * * * *